(12) United States Patent
Shin et al.

(10) Patent No.: US 10,049,617 B2
(45) Date of Patent: Aug. 14, 2018

(54) DISPLAY DEVICE HAVING REDUCED POWER CONSUMPTION AND DRIVING METHOD THEREFOR

(71) Applicant: SAMSUNG DISPLAY CO., LTD., Yongin-si, Gyeonggi-do (KR)

(72) Inventors: Won Ju Shin, Yongin-si (KR); Si Beak Pyo, Yongin-si (KR)

(73) Assignee: SAMSUNG DISPLAY CO., LTD. (KR)

( * ) Notice: Subject to any disclaimer, the term of this patent is extended or adjusted under 35 U.S.C. 154(b) by 0 days.

(21) Appl. No.: 15/237,201

(22) Filed: Aug. 15, 2016

(65) Prior Publication Data

US 2017/0053592 A1 Feb. 23, 2017

(30) Foreign Application Priority Data

Aug. 21, 2015 (KR) ........................ 10-2015-0118200

(51) Int. Cl.
*A61B 5/0402* (2006.01)
*G06F 3/041* (2006.01)
(Continued)

(52) U.S. Cl.
CPC ........... *G09G 3/3225* (2013.01); *G06F 3/011* (2013.01); *G09G 3/20* (2013.01); *G09G 3/3648* (2013.01);
(Continued)

(58) Field of Classification Search
CPC ........... G09G 3/3406; G09G 2330/021; G09G 2320/0247; G09G 3/3611;
(Continued)

(56) References Cited

U.S. PATENT DOCUMENTS 8,947,406 B2 * 2/2015 Wakimoto ........... G09G 3/3648
345/204
2004/0171956 A1 * 9/2004 Babashan .......... A61B 5/02438
600/509

(Continued)

FOREIGN PATENT DOCUMENTS

EP 2284826 A1 2/2011
EP 2876636 A1 5/2015
KR 10-2014-0147300 A 12/2014

OTHER PUBLICATIONS

Partial European Search Report for EP Patent Application No. 16185001, dated Nov. 18, 2016, 8 pages.

(Continued)

*Primary Examiner* — Duc Q Dinh
(74) *Attorney, Agent, or Firm* — Innovation Counsel, LLP (57) ABSTRACT

A display device may include a display panel, a data driver transmitting a data signal, a scan driver sequentially transmitting a scan signal, a frequency selector for selecting a driving frequency for image display, selecting a low frequency if the image displayed on the display panel is a first image and selecting a normal frequency if the image displayed on the display panel is not the first image, the normal frequency being higher than the low frequency. The display device also includes a timing controller for controlling the data driver and the scan driver based on the selected driving frequency. The timing controller may control the data driver and the scan driver such that luminance of the display panel on which the first image is displayed is periodically changed according to the low frequency if the image displayed on the display panel is the first image.

12 Claims, 4 Drawing Sheets (51) Int. Cl.
*G09G 3/3225* (2016.01)
*G09G 3/20* (2006.01)
*G06F 3/01* (2006.01)
*G09G 3/36* (2006.01)
*A61B 5/024* (2006.01)
*G09G 5/10* (2006.01)

(52) U.S. Cl.
CPC ............ *A61B 5/024* (2013.01); *G09G 3/2003* (2013.01); *G09G 5/10* (2013.01); *G09G 2310/08* (2013.01); *G09G 2320/0247* (2013.01); *G09G 2320/062* (2013.01); *G09G 2320/0626* (2013.01); *G09G 2320/103* (2013.01); *G09G 2330/021* (2013.01); *G09G 2330/022* (2013.01); *G09G 2340/045* (2013.01); *G09G 2340/0435* (2013.01); *G09G 2340/14* (2013.01); *G09G 2354/00* (2013.01); *G09G 2380/08* (2013.01)

(58) Field of Classification Search
CPC ..... G09G 2360/144; G09G 2320/0626; G09G 2320/066; G09G 2320/0233; G09G 2320/062; G09G 2320/103; G09G 5/10; G09G 2310/08; G09G 2380/08; A61B 5/021; A61B 5/02438; A61B 5/02405; A61B 5/681; A61B 5/486; A61B 5/02055; A61B 5/024; A61B 5/742; A61B 5/0205; A61B 5/0482; A61B 8/02; A61B 5/6824; A61B 5/6826
USPC ..................... 345/87, 98–100, 102, 173–175
See application file for complete search history.

(56) References Cited

U.S. PATENT DOCUMENTS

| | | |
|---|---|---|
| 2008/0309652 A1 | 12/2008 | Ostlund |
| 2009/0128487 A1 | 5/2009 | Langereis |
| 2012/0013552 A1* | 1/2012 | Ahn .................... G06F 3/04847 345/173 |
| 2013/0111377 A1 | 5/2013 | Newman |
| 2014/0375627 A1 | 12/2014 | Kim et al. |
| 2015/0062100 A1* | 3/2015 | Tanaka ................ G09G 3/3648 345/204 |
| 2015/0082446 A1* | 3/2015 | Flowers ................ G06F 3/0488 726/26 |

OTHER PUBLICATIONS

Extended European Search Report for EP Patent Application No. 16185001.1, dated Mar. 1, 2017.

* cited by examiner

| Mon, 10 March | 12:45 PM | ⊙ 06:30 AM |

DISPLAY DEVICE HAVING REDUCED POWER CONSUMPTION AND DRIVING METHOD THEREFOR

CROSS-REFERENCE TO RELATED APPLICATION

This application claims priority to, and the benefit of, Korean Patent Application No. 10-2015-0118200 filed on Aug. 21, 2015 in the Korean Intellectual Property Office, the entire content of which is incorporated herein by reference in its entirety.

BACKGROUND

1. Field

Embodiments relate generally to display devices. More specifically, embodiments relate to display devices having reduced power consumption and associated driving methods.

2. Description of the Related Art

Display devices today are employed in widely used computer monitors, televisions, mobile phones or the like. Such display devices may include a cathode-ray tube, liquid crystal, plasma, organic light emitting display devices, or the like.

These display devices typically include a display panel and a signal controller. The signal controller generates a control signal to drive the display panel along with an image signal received from an external source, and transmits them to the display panel.

High-frequency driving techniques have been developed in order to eliminate motion blur, afterimage, and flicker, causes for a decline in picture quality. Accordingly, breaking from the traditional 60 Hz driving technology, high frequency driving technologies such as 120 Hz, 240 Hz, 480 Hz, etc. are being developed to realize high picture quality.

However, unlike TV which uses commercial electricity, mobile devices such as mobile phones and information technology products are sensitive to power consumption because they are supplied with power through a battery.

Therefore, a technology to prevent a decline in picture quality due to causes such as motion blur, afterimage and flicker, and to reduce power consumption, should be developed.

SUMMARY

Embodiments relate to a display device that reduces power consumption and solves flicker problems by driving a first image at a low frequency, as well as a method for driving the same.

In accordance with an embodiment, a display device may include a display panel including a plurality of pixels coupled to scan lines and data lines, a data driver coupled to the data lines and configured to transmit a data signal, a scan driver coupled to the scan lines and configured to sequentially transmit a scan signal, a frequency selector for selecting a driving frequency for display of an image, the frequency selector further configured to select a low frequency if the image displayed on the display panel is a first image and to select a normal frequency if the image displayed on the display panel is not the first image, the normal frequency being higher than the low frequency, and a timing controller for controlling the data driver and the scan driver based on the driving frequency selected by the frequency selector. The timing controller may control the data driver and the scan driver such that luminance of the display panel on which the first image is displayed is periodically changed according to the low frequency if the image displayed on the display panel is the first image.

Also, the low frequency may comprise repeating cycles, where the timing controller may change the luminance from a first luminance value to a second luminance value in continuous manner during each cycle of the low frequency.

Also, the timing controller, if the first image comprises at least any one of a text or an included image, may change a size or a color of the text or the included image every said cycle.

Also, the first image may be an always on display (AOD) image for displaying certain information on the display panel at all times even though an input signal for activating the display panel is not detected.

Also, the certain information may include at least any one of present time, date, weather, location of user, biological information or an alarm message.

Also, if the first image includes a clock screen showing the present time, the frequency selector may set the low frequency to 1 Hz.

Also, the display device may further include a biological information receiving unit for receiving information relating to a heart rate of the user. The frequency selector may select the low frequency to correspond to the heart rate of the user.

Also, the normal frequency may be 60 Hz, and the low frequency may be 0 Hz or greater and 3 Hz or less.

Also, if the low frequency is 0 Hz, the timing controller may lower the luminance from a first luminance value to a second luminance value in continuous manner when the first image is displayed on the display panel and thereafter maintain the second luminance value.

The display device may further include a touch sensor for generating a touch input signal. The timing controller may increase the luminance to the first luminance value in response to the touch input signal.

In accordance with another embodiment, a method of driving a display device may include determining a type of image to be displayed on a display panel, selecting a driving frequency for driving display of the image, the selecting comprising selecting a low frequency as the driving frequency if the image to be displayed on the display panel is a first image and selecting a normal frequency as the driving frequency if the image to be displayed on the display panel is not the first image, and displaying the image on the display panel based on the selected driving frequency, the displaying further comprising repetitively changing a luminance of the first image in every cycle of the low frequency if the image is the first image.

Also, the displaying the image may further include gradually changing the luminance from the first luminance value to the second luminance value during the cycles if the image is the first image.

Also, the displaying the image may further comprise changing at least any one of a size or a color of a text or a graphical image included in the first image from one cycle to the next cycle if the image is the first image.

Also, the method may further include receiving information relating to a heart rate of the user from a terminal measuring biological information of the user. If the image is the first image, a low frequency value corresponding to the heart rate of the user may be selected as the driving frequency.

Also, the first image may be an always on display (AOD) image for displaying certain information on the display panel at all times even though an input signal for activating the display panel is not detected.

In an embodiment, power consumption may be reduced by driving the first image at a low frequency.

Also, the problem of flicker due to low frequency operation may be resolved, or utilized to advantage.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. The various figures are thus not necessarily to scale. It will be understood that when an element is referred to as being "between" two elements, it can be the only element between the two elements, or one or more intervening elements may also be present. Like reference numerals refer to like elements throughout.

DETAILED DESCRIPTION

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. In addition, it will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section, a second element, component, region, layer or section could be termed a first element, component, region, layer or section, and so forth, without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. All numerical values are approximate, and may vary. All examples of specific materials and compositions are to be taken as nonlimiting and exemplary only. Other suitable materials and compositions may be used instead.

Figure 1:
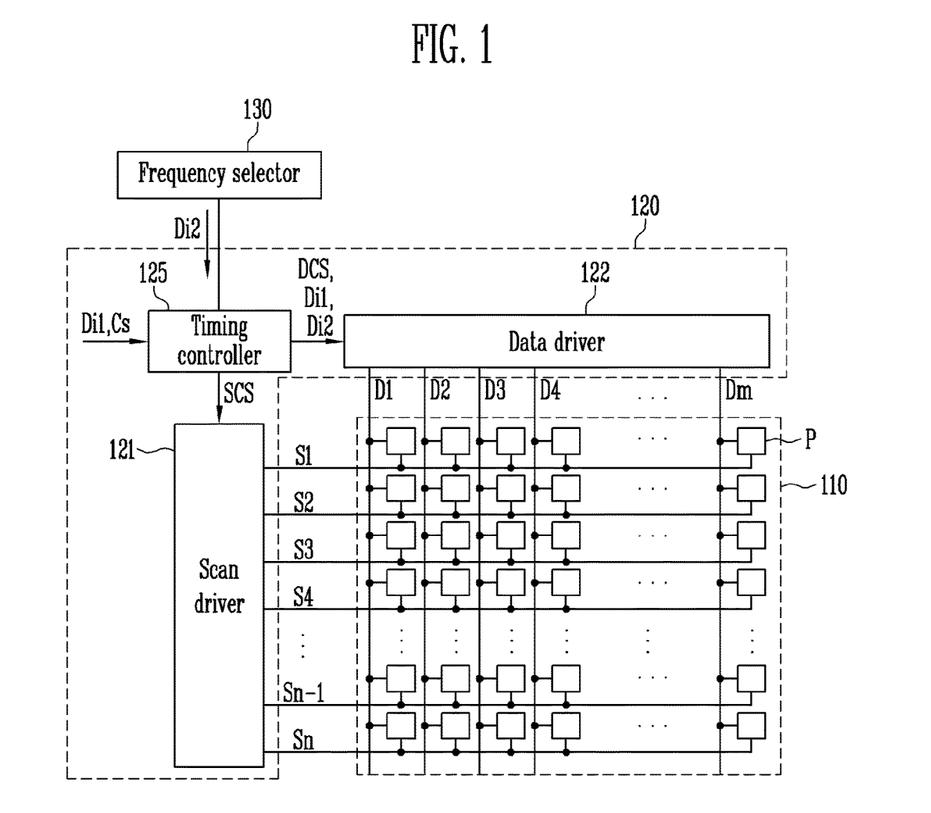
FIG. 1 illustrates a display panel, a display driver, and a frequency selector in accordance with an embodiment.

FIG. 1 illustrates a display panel 110, a display driver 120, and a frequency selector 130 in accordance with an embodiment.

A display device in accordance with an embodiment, as shown in FIG. 1, may include a display panel 110 for displaying image, a data driver 122 and a scan driver 121 for driving the display panel 110. The display may also include a timing controller 125, and a frequency selector 130 for controlling the data driver 122 and the scan driver 121.

Referring to FIG. 1, the display panel 110 may include multiple data lines D1 to Dm, multiple scan lines S1 to Sn, and multiple pixels P.

The multiple scan lines S1 to Sn may extend in a horizontal direction, and the multiple data lines D1 to Dm may extend in a vertical direction, crossing the multiple scan lines S1 to Sn.

The pixels P may be coupled to the data lines D1 to Dm and the scan lines S1 to Sn. For example, the pixels P may be arranged in matrix form at the intersections of the data lines D1 to Dm and the scan lines S1 to Sn.

Also, each pixel P may receive a data signal and a scan signal through the data lines D1 to Dm and the scan lines S1 to Sn.

Embodiments may be applied to various display panels, such as liquid crystal display panels, organic light emitting display panels, electrophoretic display panels, plasma display panels, or the like.

The display driver 120 may include the scan driver 121, the data driver 122, and the timing controller 125. In addition, a driving signal generated by the display driver 120 may include a scan signal and a data signal.

The scan driver 121 may supply scan signals to the scan lines S1 to Sn in response to timing control signals SCS. For example, the scan driver 121 may sequentially supply scan signals to the scan lines S1 to Sn.

The scan driver 121 may be electrically coupled to the scan lines S1 to Sn located on the display panel 110 through a separate component. Or the scan driver 121 may be mounted directly on the display panel 110.

The data driver 122 may receive data timing control signals DCS and image data Di1 and Di2 from the timing controller 125, and may generate data signals in response. Also, the data driver 122 may supply the generated data signals to the data lines D1 to Dm.

The data driver 122 may be electrically coupled to the data lines D1 to Dm located on the display panel 110 through a separate component. Or the data driver 122 may be mounted directly on the display panel 110.

The pixels P is supplied with data signals through the data lines D1 to Dm and may emit light at a luminance corresponding to the data signals. More specifically, the data driver 122 may display images by supplying data signals corresponding to the image data Di1 and Di2.

The data driver 122, as shown in FIG. 1, may be located separately from the scan driver 121. However, in another embodiment, the data driver 122 may be integrated into the scan driver 121.

The timing controller 125 may receive image data Di1 and a control signal Cs from an external source.

The timing controller 125 may generate timing control signals to control the scan driver 121 and the data driver 122 based on the control signal Cs.

For example, the timing control signals may include a scan timing control signal SCS to control the scan driver 121 and a data timing control signal DCS to control the data driver 122.

Therefore, the timing controller 125 may supply a scan timing control signal SCS to the scan driver 121 and a data timing control signal DCS to the data driver 122.

In addition, the timing controller 125 may receive image data Di2, which includes information regarding a driving frequency (frequency to drive the display panel), from the frequency selector 130.

For example, the timing controller 125, referring to the image data Di2 transmitted from the frequency selector 130, may operate in such a way that the first image driven at a low frequency may be displayed on the display panel 110, or the second image driven at a normal frequency may be displayed.

Here, the timing controller 125 may convert the image data Di1 and Di2 such that the image data Di1 and Di2 are suitable for the specifications of the data driver 122, and supply them to the data driver 122.

FIG. 1 shows the frequency selector 130 as being located separately from the timing controller 125, but it is not so limited, and unlike what is shown in FIG. 1, the frequency selector 130 may be integrated into the timing controller 125.

Figure 2:
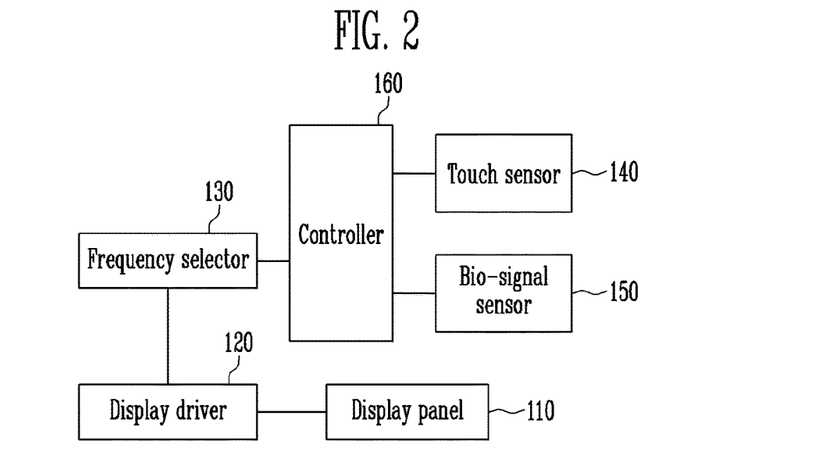
FIG. 2 is a block diagram schematically illustrating an internal configuration of a display device in accordance with an embodiment.

FIG. 2 is a block diagram illustrating the internal configuration of a display device in accordance with an embodiment.

Referring to FIG. 2, a display device in accordance with an embodiment may include a display panel 110, a display driver 120, a frequency selector 130, a touch sensor 140, a bio-signal sensor 150, and a controller 160.

First, the touch sensor 140 may detect a touch by a user, and more specifically, a touch by a body part of the user (for example, a finger) or by a stylus or the like.

Touches by the user may be performed by a direct touching action of a finger, etc. on an electronic device having a display device, and by a hovering action of a finger, etc. in which a finger, etc. may approach but not physically contact the electronic device.

For example, the touch sensor 140 may be realized with any one or more of a capacitive type touch sensor, a resistive type touch sensor, an optical touch sensor, a surface acoustic wave touch sensor, a pressure touch sensor, or a hybrid touch sensor.

Here, a hybrid touch sensor may be realized by combining the same type of sensors together, or by combining different types of sensors together.

However, the touch sensor 140 used in an embodiment is not limited to the types mentioned above; regardless of the type, a sensor capable of detecting touch by a finger or a tool is sufficient.

The touch sensor 140 may generate and supply a touch signal to a touch controller (not shown) when touch by the user is detected.

The touch controller may detect the location of touch using a touch signal supplied from the touch sensor 140.

The touch sensor 140, as shown in FIG. 2, may be located separately from the display panel 110, but is not limited thereto, and the touch sensor 140 may alternatively be integrated into the display panel 110.

Next, the bio-signal sensor 150 may perform the function of obtaining a user's biometrics information from a biometrics measuring device (not shown).

Biometrics information may include at least one of blood pressure, blood sugar, heart rate (or pulse), body fat, weight, the presence of diseases such as atopic dermatitis, asthma, etc., stress level, organic compounds in exhalation, or height.

The biometrics measuring device may measure the user's biometrics, which may include not only a blood pressure measuring device, a blood sugar measuring device, a pulse measuring device, or a weight measuring device, but also a height measuring device, a body temperature measuring device, and the like.

Also, the biometrics measuring device may include various measuring devices which measure factors affecting the user's health and those attributes of the surrounding environment which may affect the user's health (for example, temperature, humidity, ultraviolet index, cleanliness, etc.).

Next, the controller 160 may control the flow of data among the touch sensor 140, the bio-signal sensor 150, and the frequency selector 130. In other words, the controller 160 may operate in such a way that the touch sensor 140, the bio-signal sensor 150, and the frequency selector 130 each may perform its unique functions, by controlling the flow of data between components.

In FIG. 2, the controller 160 is shown to be located separately from each component for ease of illustration, but it is not limited thereto and may instead for example be combined into the frequency selector 130, or into the timing controller 125 along with the frequency selector 130.

Next, the display panel 110 may display certain images by including multiple pixels P as described in detail with reference to FIG. 1. For example, the display panel 110 may display the first image or the second image in accordance with the control of the display driver 120.

Also, the display panel 110 may be realized with an organic light emitting display panel, a liquid crystal display panel, a plasma display panel, etc., but is not limited thereto. Any display is contemplated.

The display driver 120 may control the image display actions of the display panel 110 by supplying certain driving signals to the display panel 110.

For example, the display driver 120 may generate a driving signal using at least one of the following: the image data Di1 supplied from an external source, the image data Di2 for a driving frequency in accordance with a selection by the frequency selector 130, and the control signal Cs.

Specifically, the display driver 120 may display the first image or the second image on the display panel 110. When the image displayed on the display panel 110 is the first image, a driving signal may be generated such that the luminance of the display panel on which the first image is displayed may repeatedly change every cycle corresponding to a low frequency selected by the frequency selector 130.

Next, the frequency selector 130 may select a driving frequency for display of the image. Especially when the image displayed on the display panel 110 is the first image, the frequency selector 130 may select a low frequency, and when the image displayed on the display panel 110 is the second image, the frequency selector 130 may select a normal frequency that is higher than the low frequency.

An image displayed on the display panel 110 which is not a first image shall be referred to as a second image.

The first image may be an Always On Display (AOD) image to display certain information on the display panel 110 at all times, even when an input signal to activate the display panel 110 is not detected. This is in contrast to images which appear when the display panel 110 is activated in accordance with the user's need.

Here, the certain information displayed in the first image may include at least one of the following: the present time, the date, the weather, the user's location, the user's biometrics, or notification messages. For example, the first image may include a clock screen or the like.

An input signal to activate the display panel 110 may be a touch input signal, or a signal by an input button of an electronic device equipped with a display device in accordance with an embodiment.

When displaying the first image, that is, an AOD image, it may be advantageous to be able to check certain information at all times, and this may be especially useful for wearable display devices, smart phones, etc. which must display fixed screens for long periods of time.

However, because the first image is always on, there may be a problem of power consumption, but such a problem may be solved by driving the first image at a low frequency. This will be described subsequently.

Generally the display panel 110 displays several frames per second. For example, when the driving frequency of the display panel 110 is 60 Hz, it may display 60 frames per second, and when the driving frequency is 1 Hz, it may display one frame per second.

When the image data of each frame is the same, a still image may be displayed, and when the image data of each frame is different, video or moving images may be displayed.

As each pixel P on the display panel 110 emits light, voltage charged in a capacitor (not shown) in each pixel P may decrease over time, and especially when driven at a low frequency, the amount of time it takes for the voltage to leak may increase, leading to an increased voltage difference of a pixel electrode.

Therefore, in this case, the phenomenon of flicker may be perceived. Conventionally, the phenomenon of flicker may be controlled by driving at a high frequency even when a still image is displayed, such that the problem of flicker may not be perceived.

Therefore, in an embodiment, when the image displayed on the display panel 110 is the first image, power consumption may be reduced by operating at a low frequency and may solve any user inconveniences arising from flicker.

The frequency selector 130 may select a low frequency as a driving frequency of the display panel 110 when the image displayed on the display panel 110 is the first image. Specifically, it may select a frequency corresponding to either a second (i.e. 1 sec) or the heart rate of the user.

The timing controller 125 may control the display panel 110 based on a driving frequency selected by the frequency selector 130, such that the luminance of the first image is changed repeatedly every cycle corresponding to the driving frequency when the image displayed on the display panel 110 is the first image.

This will be described subsequently with reference to FIG. 3.

Figure 3:
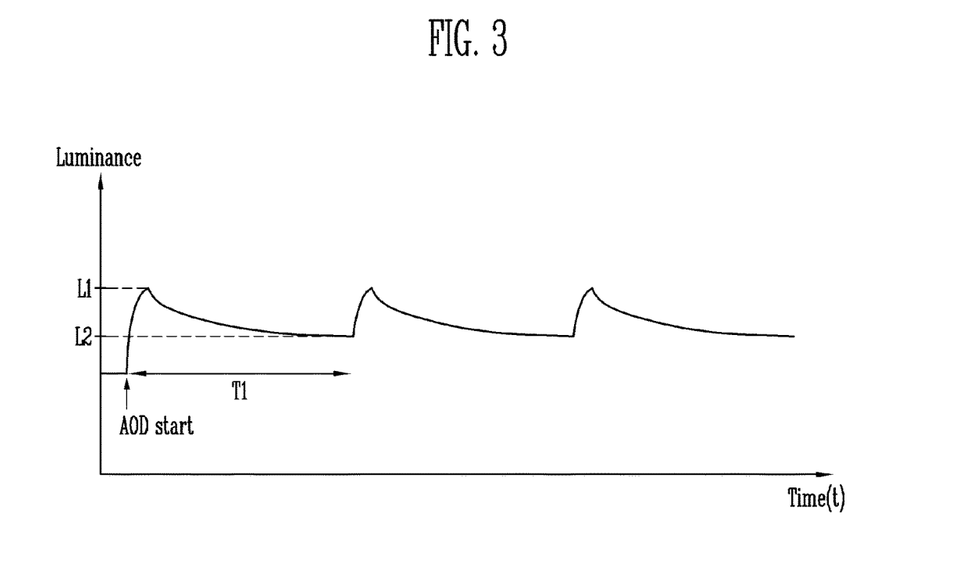
FIG. 3 illustrates changes in the luminance of a first image displayed on a display panel in accordance with an embodiment.

FIG. 3 illustrates changes in the luminance of a first image displayed on a display panel in accordance with an embodiment.

As shown in FIG. 3, the luminance of the first image may be changed repeatedly every certain cycle T1 by a driving frequency selected by a frequency selector 130 and a control signal of a timing controller 125.

In other words, when the first image starts, during one cycle T1, the luminance of the first image may increase to the value of a first luminance value L1 and then continuously decay from the first luminance value L1 to a second luminance value L2 in an analog manner. After one cycle, when a new cycle begins, the luminance of the first image may increase to the first luminance value L1 again, and then once again decay from the first luminance value L1 to the second luminance value L2 in an analog manner.

For example, when the frequency selector 130 selects 1 Hz corresponding to 1 second, which is the unit with which the frequency selector 130 measures time as a driving frequency, the luminance of the first image may be changed every second.

As described above, the first image in accordance with an embodiment may be AOD, which, unlike a simple still image, contains information regarding time, date, location, biometrics, etc. that may continuously change, e.g. a clock screen.

In other words, in accordance with an embodiment, in displaying the first image including a clock screen, the phenomenon of flicker due to low frequency driving may be utilized as a new function (for example, a stopwatch) by causing flickering by changing the luminance every second.

Meanwhile, as described above, the frequency selector 130 may select, as a driving frequency, a low frequency value corresponding to a heart rate of the user.

In this case, the frequency selector 130 may obtain the user's heart rate (number of heartbeats per minute) from the bio-signal sensor 150. For example, when the user's heart rate is 80, the luminance of the first image may be changed every 0.75 seconds (or value proportional to 0.75).

In an embodiment, as the user's heart rate goes up, the cycle T1 may shorten. Therefore, the user may estimate his/her own heart rate based on the rate at which the display panel 110 flickers.

In other words, in an embodiment, driving the first image at a low frequency may lead to lower power consumption, and the phenomenon of flicker may be solved by using the problem of voltage leakage due to low frequency operation to convey useful information to the user.

In an embodiment, when the first image is displayed, low frequency values which the frequency selector 130 selects may be 0 Hz or greater and 3 Hz or less, such that a driving frequency of the display panel 110 may correspond to a unit of time (especially the second) or the heart rate of the user. Also, when the second image is displayed, the display panel may be driven at 60 Hz, which is a conventional driving frequency. It should be noted that 60 Hz is described herein as a normal or conventional frequency, but the driving frequency is not limited thereto, and the value of a normal frequency which displays the second image may vary depending on the specification of the display device.

In FIG. 3, it is assumed that the value of the first luminance L1 is greater than the value of the second luminance L2 and gradually decreases over one cycle, but it is not limited thereto.

It is also possible to set the value of the first luminance L1 to be smaller than the value of the second luminance L2, such that luminance may increase over one cycle.

Figure 4:
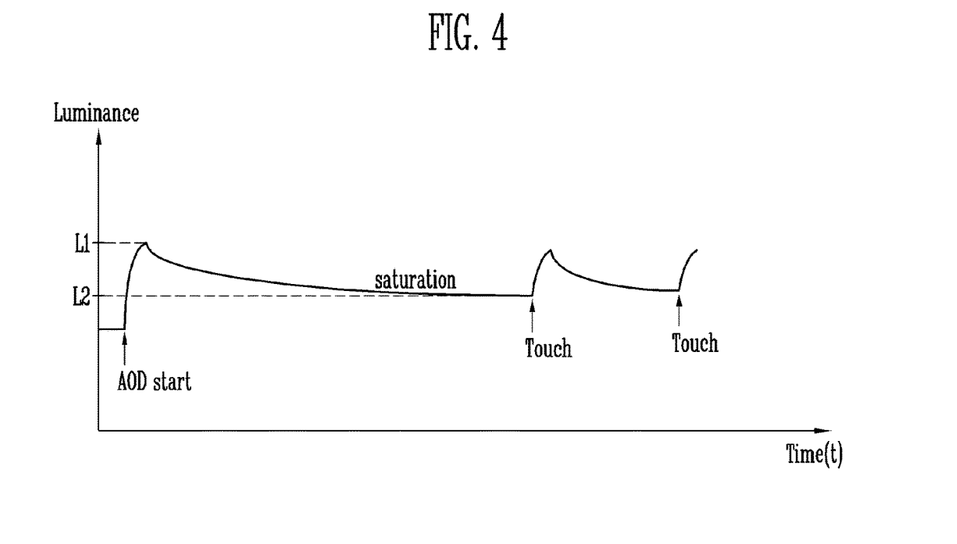
FIG. 4 illustrates changes in the luminance of a first image displayed on a display panel in accordance with another embodiment.

Detailed explanations will follow regarding, in displaying the first image, changes in the luminance of the first image when a low frequency selected by the frequency selector 130 is 0 Hz.

FIG. 4 illustrates changes in the luminance of a first image displayed on a display panel 110 in accordance with another embodiment.

Unlike an embodiment in which the luminance of the first image is changed or refreshed repeatedly from the first luminance value L1 to the second luminance value L2 in an analog manner, referring to FIG. 4, the luminance of the first image may continuously decrease from the first luminance value L1 in an analog manner, without being refreshed at predetermined time intervals.

In this case, when the value of the luminance reaches the second luminance value L2, the luminance of the first image may still maintain the second luminance value L2 even after time has expired. In other words, it may be saturated at the second luminance value.

As shown in FIG. 4, when the luminance of the first image is decreasing from the first luminance value, or when a certain amount of time has passed and the luminance of the first image is saturated at the second luminance value L2, the luminance of the first image may increase back to the first luminance value L1 every time a touch input signal is detected. That is, the luminance of the first image may be refreshed to first luminance value L1 upon a touch, not at any particular time or time interval.

Referring to FIGS. 5 to 8, examples shall be given hereunder of display devices in accordance with embodiments and as used in various electronic devices.

Figure 5:
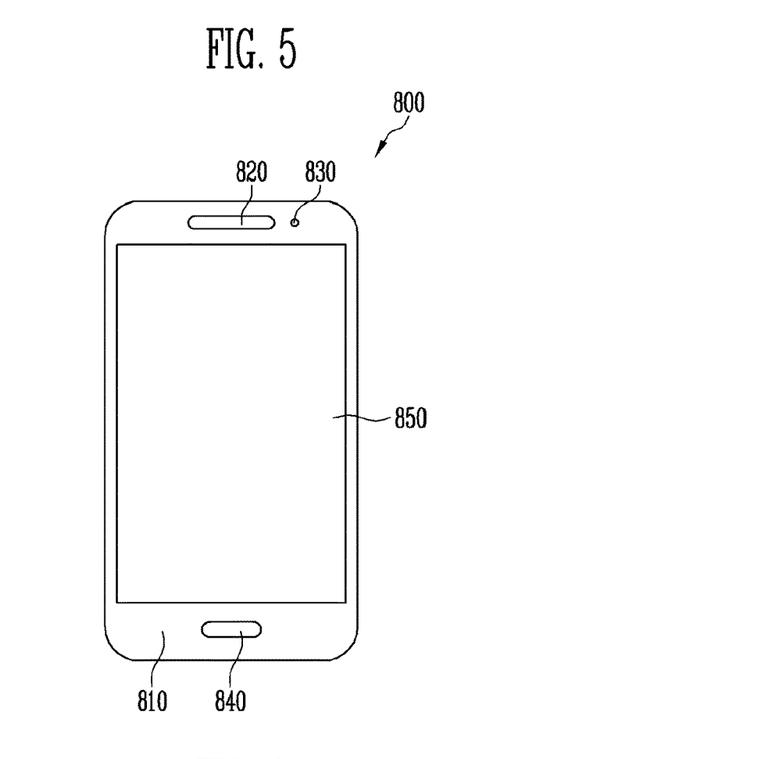
FIG. 5 illustrates the appearance of electronic equipment with a display device in accordance with an embodiment.

FIG. 5 illustrates an exemplary electronic device including a display device in accordance with an embodiment.

Referring to FIG. 5, an electronic device 800 in accordance with an embodiment may include a display device 850 for displaying images, a main body 810 to which the display device is stably placed and locked of affixed, an additional device formed on the main body 810 for performing certain functions, etc.

The additional device may include a physical button 840, an audio part 820, a front camera module 830, or the like.

Figure 6:
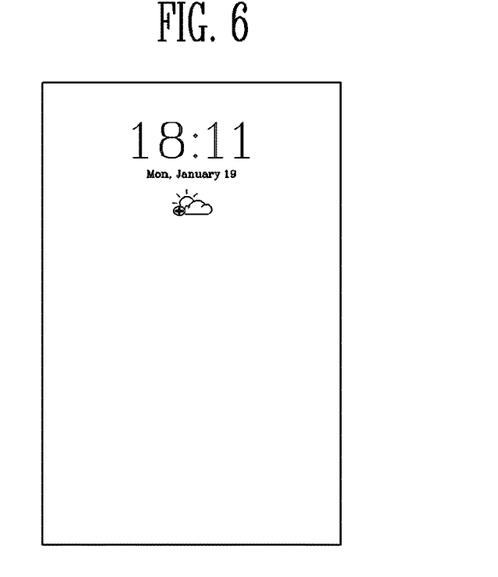
FIG. 6 illustrates a first image in accordance with an embodiment being displayed on the electronic equipment shown in FIG. 5 as an example.

FIG. 6 illustrates an example of a first image in accordance with an embodiment, being displayed on the electronic device shown in FIG. 5.

As shown in FIG. 5 and FIG. 6, a display device 850 in accordance with an embodiment may be flat and display a first image on certain areas of the display device 850.

Text indicating the present time, day, and date and an image indicating the weather may be displayed together in the first image.

As described above, the luminance of the first image shown in FIG. 6 may be changed every certain cycle. Also, not only the luminance of the first image, but also the sizes or colors of the text and the image displayed in the first image may be changed as well.

For example, at least one of either the size or the color of the text and the image may be changed every time T1 passes, or every time the first image is refreshed.

When the first image is displayed on the display device 850 in accordance with an embodiment, the remaining display panel area other than the area on which the first image is displayed may be set not to emit light, in order to reduce power consumption.

In FIG. 5, the electronic device 800 is shown to be a smart phone for ease in illustration, but it is not limited thereto, and a smart watch, display for automobiles, etc. may also be adopted to be the electronic device 800 in accordance with an embodiment. That is, the electronic device 800 may be any device capable of displaying an image.

Figure 7:
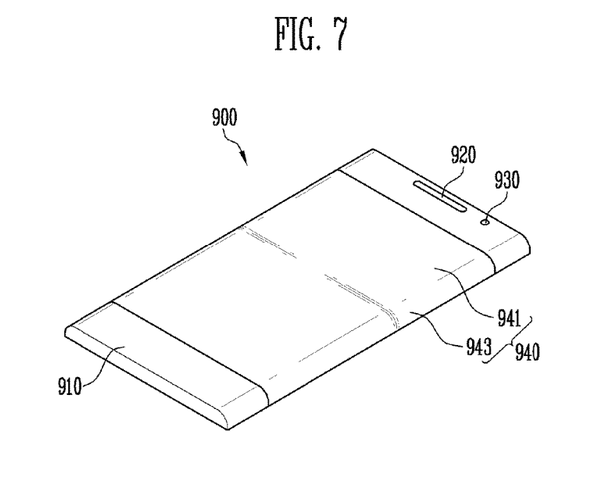
FIG. 7 illustrates the appearance of another electronic equipment in accordance with an embodiment.

FIG. 7 illustrates the appearance of an electronic device including a flexible display device in accordance with an embodiment.

Referring to FIG. 7, an electronic device 900 in accordance with an embodiment may include a flexible display device 940, a main body 910 to which the flexible display device 940 is stably placed and locked, an additional device formed on the main body 910 and for performing certain functions, or the like.

The additional device may include a speaker 920, a microphone (not shown), a front camera module 930, a physical button (not shown), or the like.

The flexible display device 940 may refer to a display device which can bend, and may bend or be rolled due to its paper-like thin and flexible substrate.

Since a flexible display device 940 like this uses a plastic substrate, not a glass substrate as generally used, it may be formed using a low-temperature manufacturing process instead of a conventional manufacturing process, in order to prevent damage to the substrate.

In a flexible display device 940, the glass substrate surrounding the liquid crystals in a liquid crystal display LCD, light emitting diodes LED, organic LED OLED, active matrix OLED AMOLED, etc. may be replaced by plastic film, making it flexible enough to be folded and unfolded.

The flexible display device 940 may not only be thin and light but also strong against shock, may bend or be folded, and may be manufactured in various forms or shapes.

As shown in FIG. 7, the flexible display device 940 may extend to and over at least one side (for example, at least one side among left, right, upper, and bottom) of the electronic device 900, folded enough to clear out of the operable radius of curvature of the flexible display device 940, and locked on or attached to a side of the main body 910.

Hereunder, the display area on the front side of the flexible display device 940 may be referred to as a main display area 941, and the display area extending from the main display area 941, curving to at least one side of the main body 910, and appearing on the side of the main body 910 may be referred to as an auxiliary display area 943.

In an embodiment, as described with reference to FIGS. 5 and 6, the first image may be displayed on the front side of the display area, that is, on the main display area 941, but when a flexible display device 940 as shown in FIG. 7 is equipped, the first image may also (or alternatively) be displayed on the auxiliary display area 943.

Figure 8:
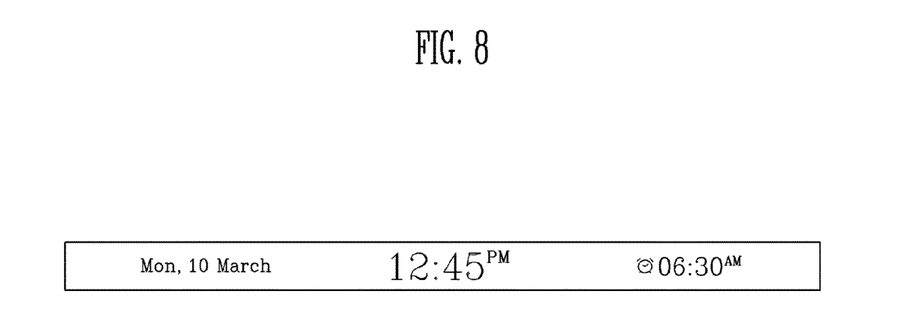
FIG. 8 illustrates a first image in accordance with an embodiment being displayed on the electronic equipment shown in FIG. 7 as an example.

FIG. 8 illustrates examples of a first image in accordance with an embodiment, being displayed in the auxiliary display area 943 of the electronic device 900 shown in FIG. 7.

In an embodiment, the first image may be displayed using the auxiliary display area 943. In this case, even when the electronic device 900 is put into a separate case (not shown) covering the main display area 941, certain information may still be provided through the auxiliary display area 943. This information may, if desired, be displayed at any or all times.

As shown in FIG. 8, a text and a certain image indicating present time, day, date, and alarms may be displayed together in the first image, although any information capable of display is contemplated.

The first video shown in FIG. 8 may be changed every certain cycle, and not only the luminance of the first video, but also the size or the color of the text and the image displayed in the first video may be changed together. Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims. Various features of the above described and other embodiments can be mixed and matched in any manner, to produce further embodiments consistent with the invention.

What is claimed is:

1. A display device comprising:
a display panel comprising a plurality of pixels coupled to scan lines and data lines;
a data driver coupled to the data lines and configured to transmit a data signal;
a scan driver coupled to the scan lines and configured to sequentially transmit a scan signal;
a biological information receiver configured to receive information relating to a heart rate of a user;
a frequency selector configured to select a driving frequency for displaying an image, the frequency selector further configured to select a low frequency if the image displayed on the display panel is a first image and to select a normal frequency if the image displayed on the display panel is not the first image, the normal frequency being higher than the low frequency; and
a timing controller configured to control the data driver and the scan driver based on the driving frequency selected by the frequency selector,
wherein the timing controller controls the data driver and the scan driver such that luminance of the display panel on which the first image is displayed is periodically changed according to the low frequency if the image displayed on the display panel is the first image, and
wherein the frequency selector selects the low frequency to correspond to the heart rate of the user.

2. The display device as claimed in claim 1, wherein the low frequency comprises repeating cycles, and wherein the timing controller changes the luminance from a first luminance value to a second luminance value in continuous manner during each cycle of the low frequency.

3. The display device as claimed in claim 1, wherein the timing controller, if the first image comprises at least any one of a text or an included image, changes a size or a color of the text or the included image every said cycle.

4. The display device as claimed in claim 1, wherein the first image is an always on display (AOD) image for displaying certain information on the display panel at all times even though an input signal for activating the display panel is not detected.

5. The display device as claimed in claim 4, wherein the certain information includes at least any one of present time, date, weather, location of user, biological information or an alarm message.

6. The display device as claimed in claim 1, wherein the normal frequency is 60 Hz, and wherein the low frequency is 0 Hz or greater and 3 Hz or less.

7. The display device as claimed in claim 6, wherein if the low frequency is 0 Hz, the timing controller lowers the luminance from a first luminance value to a second luminance value in continuous manner when the first image is displayed on the display panel, and thereafter maintains the second luminance value.

8. The display device as claimed in claim 7, further comprising a touch sensor configured to generate a touch input signal, wherein the timing controller increases the luminance to the first luminance value in response to the touch input signal.

9. A method of driving a display device, the method comprising:
determining a type of image to be displayed on a display panel;
receiving information relating to a heart rate of a user from a terminal measuring biological information of the user;
selecting a driving frequency for driving display of the image, the selecting comprising selecting a low frequency which corresponds to the heart rate of the user as the driving frequency if the image to be displayed on the display panel is a first image and selecting a normal frequency as the driving frequency if the image to be displayed on the display panel is not the first image; and
displaying the image on the display panel based on the selected driving frequency, the displaying further comprising repetitively changing a luminance of the first image in every cycle of the low frequency if the image is the first image.

10. The method as claimed in claim 9, wherein the displaying the image further comprises gradually changing the luminance from the first luminance value to the second luminance value during the cycles if the image is the first image.

11. The method as claimed in claim 10, wherein the displaying the image further comprises changing at least any one of a size or a color of a text or a graphical image included in the first image from one cycle to the next cycle if the image is the first image.

12. The method as claimed in claim 9, wherein the first image is an always on display (AOD) image for displaying certain information on the display panel at all times even though an input signal for activating the display panel is not detected.

* * * * *